(12) United States Patent
Fater

(10) Patent No.: US 12,280,182 B2
(45) Date of Patent: *Apr. 22, 2025

(54) PLATELET-ACTIVATED BIOADHESIVE STENT COATING AS AN ANTI-MIGRATION MECHANISM

(71) Applicant: BOSTON SCIENTIFIC SCIMED, INC., Maple Grove, MN (US)

(72) Inventor: Michelle Fater, Worcester, MA (US)

(73) Assignee: BOSTON SCIENTIFIC SCIMED, INC., Maple Grove, MN (US)

( * ) Notice: Subject to any disclaimer, the term of this patent is extended or adjusted under 35 U.S.C. 154(b) by 869 days.

This patent is subject to a terminal disclaimer.

(21) Appl. No.: 17/494,997

(22) Filed: Oct. 6, 2021

(65) Prior Publication Data
US 2022/0023510 A1 Jan. 27, 2022

Related U.S. Application Data

(63) Continuation of application No. 16/447,472, filed on Jun. 20, 2019, now Pat. No. 11,154,643, which is a
(Continued)

(51) Int. Cl.
*A61F 2/848* (2013.01)
*A61L 31/02* (2006.01)
(Continued)

(52) U.S. Cl.
CPC ............. *A61L 31/10* (2013.01); *A61F 2/848* (2013.01); *A61L 31/028* (2013.01); *A61L 31/06* (2013.01); *A61L 31/088* (2013.01); *A61L 31/145* (2013.01); *A61L 31/148* (2013.01); *A61F 2210/0004* (2013.01); *A61F 2210/0076* (2013.01); *A61F 2250/0039* (2013.01); *A61L 2400/04* (2013.01); *A61L 2400/16* (2013.01);
(Continued)

(58) Field of Classification Search
CPC ....................................................... A61F 2/848
See application file for complete search history.

(56) References Cited

U.S. PATENT DOCUMENTS 6,312,457 B1 * 11/2001 DiMatteo ................ A61L 27/34
623/1.36
8,114,147 B2 2/2012 Wood et al.
(Continued)

FOREIGN PATENT DOCUMENTS

| WO | 0040278 A1 | 7/2000 |
| WO | 2009036014 A2 | 3/2009 |
| WO | 2013152338 A2 | 10/2013 |

OTHER PUBLICATIONS

Johanson et al; "Incidence and Risk Factors for Bilary and Pancreatic Stent Migration", Gastrointestinal Endoscopy, vol. 38, Issue 3, May 1992, pp. 341-346.
(Continued)

*Primary Examiner* — Brian A Dukert
(74) *Attorney, Agent, or Firm* — Seager, Tufte & Wickhem, LLP

(57) ABSTRACT

A stent having an inner surface and an outer surface, the stent comprising a coating composition comprising a platelet-activated adhesive on at least a portion of the outer surface thereof.

20 Claims, 7 Drawing Sheets

Related U.S. Application Data continuation of application No. 15/460,986, filed on Mar. 16, 2017, now Pat. No. 10,357,597, which is a continuation of application No. 14/639,661, filed on Mar. 5, 2015, now Pat. No. 9,642,944.

(60) Provisional application No. 61/954,192, filed on Mar. 17, 2014.

(51) Int. Cl.
| | |
|---|---|
| *A61L 31/06* | (2006.01) |
| *A61L 31/08* | (2006.01) |
| *A61L 31/10* | (2006.01) |
| *A61L 31/14* | (2006.01) |

(52) U.S. Cl.
CPC ....... *A61L 2400/18* (2013.01); *A61L 2420/02* (2013.01); *A61L 2420/08* (2013.01)

(56) References Cited

U.S. PATENT DOCUMENTS

| | | |
|---|---|---|
| 8,221,783 B2 | 7/2012 | Helmus et al. |
| 2002/0065546 A1 | 5/2002 | Machan et al. |
| 2006/0069425 A1 | 3/2006 | Hillis et al. |
| 2006/0276887 A1 | 12/2006 | Brady et al. |
| 2008/0009934 A1 | 1/2008 | Schneider et al. |
| 2009/0062927 A1 | 3/2009 | Marten et al. |
| 2009/0098176 A1 | 4/2009 | Helmus et al. |
| 2012/0035715 A1 | 2/2012 | Robida et al. |
| 2012/0123521 A1 | 5/2012 | Headley, Jr. et al. |
| 2012/0128793 A1 | 5/2012 | Miller et al. |
| 2013/0018452 A1 | 1/2013 | Weitzner et al. |
| 2013/0103162 A1* | 4/2013 | Costello ............... A61F 2/90 118/500 |

OTHER PUBLICATIONS

Ruggeri et al; "Adhesion Mechanisms in Platelet Function" Circulation Research, vol. 100, 2007, 1673-1685,.

International Search Report and Written Opinion dated May 6, 2015 for International Application No. PCT/US2015/018962.

* cited by examiner

PLATELET-ACTIVATED BIOADHESIVE STENT COATING AS AN ANTI-MIGRATION MECHANISM

CROSS-REFERENCE TO RELATED APPLICATIONS

This application is a continuation of U.S. application Ser. No. 16/447,472, filed Jun. 20, 2019; which is a continuation of U.S. application Ser. No. 15/460,986, filed Mar. 16, 2017, now U.S. Pat. No. 10,357,597; which is a continuation of U.S. application Ser. No. 14/639,661, filed Mar. 5, 2015, now U.S. Pat. No. 9,642,944; which application claims the benefit of U.S. Provisional Application No. 61/954,192, filed Mar. 17, 2014, the disclosures of which are incorporated herein by reference.

BACKGROUND OF THE INVENTION

The present invention relates generally to a coated medical device and more particularly to a coated stent. Stents, grafts, stent-grafts, vena cava filters and similar implantable medical devices, collectively referred to hereinafter as stents, are radially expandable endoprosthesis which are typically implants capable of being implanted transluminally and enlarged radially after being introduced percutaneously. Stents may be implanted in a variety of body lumens or vessels such as within the vascular system, esophagus, gastrointestinal tract, large and small intestine, biliary ducts, pancreas ducts, pulmonary and urinary tracts, etc. Stents may be used to reinforce body vessels and to prevent restenosis following angioplasty in the vascular system. Stents may also be used to open strictures. They may be self-expanding, mechanically expandable or hybrid expandable.

Stents are typically tubular members that are radially expandable from a reduced diameter configuration for delivery through a patient's body lumen to an expanded configuration once deployed at the treatment site.

Stents may be constructed from a variety of materials such as stainless steel, Elgiloy®, nickel, titanium, nitinol, shape memory polymers, other polymeric materials, etc. For metallic stents, a stent may be typically braided or woven from singular or multiple filaments in the form of a tubular member, either extruded or formed from a sheet, in which a pattern is subsequently formed by etching or cutting material from the tubular member.

Polymeric stents formed from a variety of thermoplastic polymer materials may be formed by weaving or braiding fibers or filaments.

Stents may further be provided with a cover, such as a silicone cover to prevent tissue ingrowth.

Desirable stent properties include sufficient flexibility to be able to conform to the tortuous body lumen during delivery, yet sufficiently rigid to resist migration once deployed at the treatment site.

In some stents, the compressible and flexible properties that assist in stent delivery may also result in a stent that has a tendency to migrate from its originally deployed position. Stent covering may contribute to migration as well. Stent migration affects many endoscopic stents including esophageal, pancreatic and biliary stents. Risk factors associated with stent migration are discussed in *Incidence and risk factors for biliary and pancreatic stent migration*, Johanson J F, Schmah. M J, Geenen J E. Gastrointest Endosc. 1992 May-June; 38(3):341-6.

It is thus desirable to provide a stent configuration that resists migration following deployment.

Esophageal stents are particularly susceptible to stent migration due to the structure of the esophagus and conditions therein such as peristalsis.

Moreover, fully covered stents prevent tissue ingrowth and are easier to remove than bare or partially covered stents. However, these stents are even more prone to migration. The migration rate for a fully covered stent in pulmonary and esophageal indication is about 20-50%.

It is thus desirable to provide a stent configuration that resists migration following deployment.

One way to reduce the risk of stent migration has been to expose bare metal portions of the stent to esophageal tissue. The open structure of the stent provides a scaffold that promotes tissue ingrowth into the stent. This tissue ingrowth anchors the stent in place and greatly reduces the risk of migration. However, tissue ingrowth may lead to reocclusion of the lumen. In addition, stents anchored by tissue ingrowth cannot be moved or removed without an invasive procedure. To reduce tissue ingrowth, stents have been covered with a polymer coating to create a physical barrier between the stent lumen and the tissue wall. However, traditional polymer coated esophageal stents have higher rates of migration than their bare metal counterparts.

Another way to reduce the risk of stent migration has been to use a flared stent. However, stents are susceptible to migration even with flares.

Another method of reducing stent migration has been to provide surface features such as bumps or protrusions or other surface features such as disclosed in US Patent Publication Nos. 2006/0069425 and 2009/0062927, and in commonly assigned 2012/0035715, each of which is incorporated by reference herein in its entirety.

Commonly assigned US Patent Publication No. 2009/0098176, the entire content of which is incorporated by reference herein, discloses medical devices with triggerable bioadhesives.

Many techniques have been developed to prevent stent migration including adding barbs and flares to the stent itself or using clips or sutures to attach the stent to the vessel wall.

There remains a need in the art for an improved stent that is resistant to migration.

Without limiting the scope of the invention a brief summary of some of the claimed embodiments of the invention is set forth below. Additional details of the summarized embodiments of the invention and/or additional embodiments of the invention may be found in the Detailed Description of the Invention below.

SUMMARY OF THE INVENTION

In one aspect, the present invention relates to a stent having an inner surface and an outer surface, the stent comprising a coating composition comprising a platelet-activated adhesive on at least a portion of the outer surface thereof.

In another aspect, the present invention relates to a method of making a stent, the method comprising the steps of providing a stent having an inner surface and an outer surface and applying a platelet-activated adhesive to least to a portion of said outer surface of said stent.

These and other aspects, embodiments and advantages of the present disclosure will become immediately apparent to those of ordinary skill in the art upon review of the Detailed Description and Claims to follow.

BRIEF DESCRIPTION OF THE DRAWINGS

FIG. 3 is a cross-sectional view illustrating the stent having a platelet-activated coating thereon.

DETAILED DESCRIPTION OF THE INVENTION

While embodiments of the present disclosure may take many forms, there are described in detail herein specific embodiments of the present disclosure. This description is an exemplification of the principles of the present disclosure and is not intended to limit the disclosure to the particular embodiments illustrated.

Figure 1:
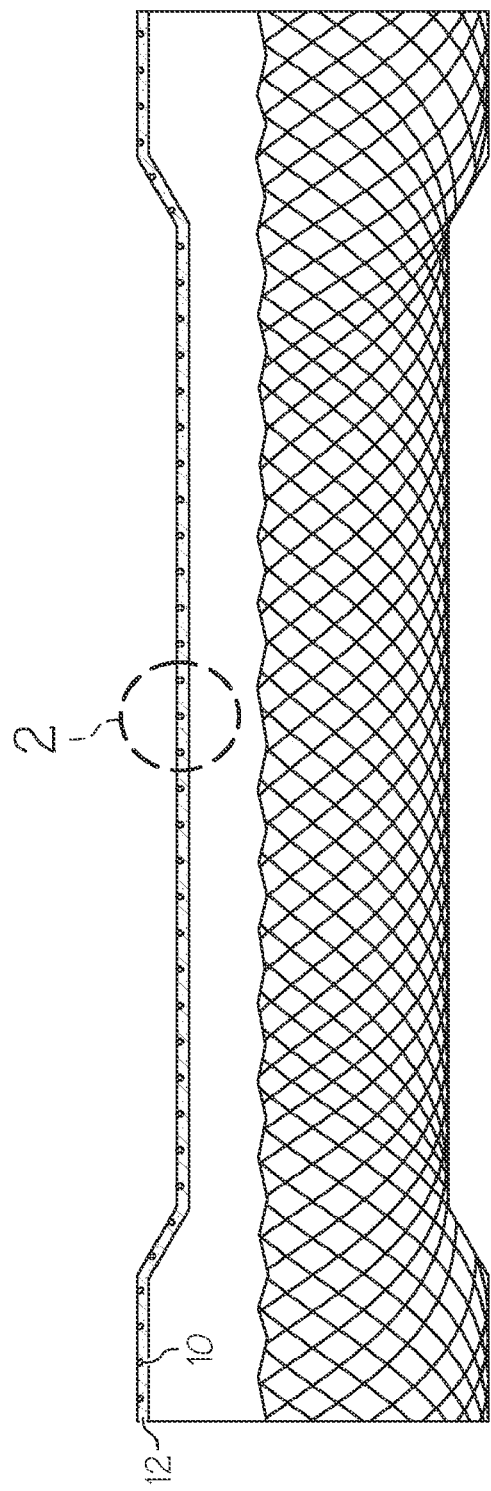
FIG. 1 is a side view of an embodiment of a stent according to the invention on which the platelet-activated adhesive may be employed.
Figure 2:
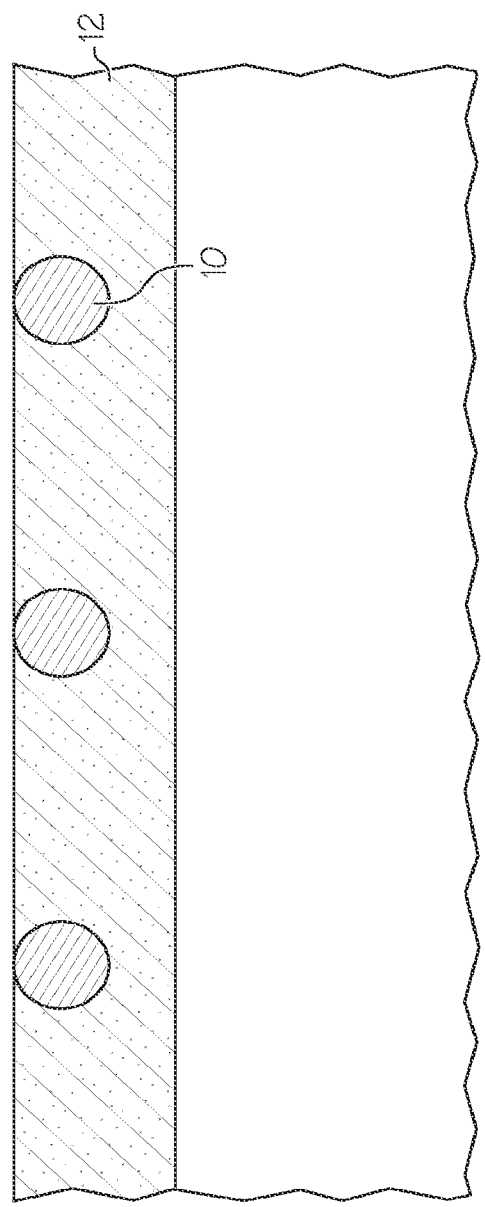
FIG. 2 is a cross-sectional view taken at 2 in FIG. 1 illustrating.

Turning now to the drawings, FIG. 1 is a side view of one embodiment of a stent on which the coatings according to the invention be employed. In this embodiment, stent 10 is a self-expanding stent formed of a shape memory metal such as nitinol having a silicone covering. The stent has a braided wire construction. In this embodiment, stent 10 is shown having a silicone covering 12. Silicone covering 12 is disposed on stent 10 and stent 10 is partially embedded therein. FIG. 2 is a partial cross-sectional view of the stent taken at section 2 in FIG. 1. Stents of this type are described in commonly assigned US Patent Publication Nos. 2006/0276887 and 2008/0009934, each of which is incorporated by reference herein in its entirety.

While in the embodiment shown in FIGS. 1 and 2, the stent is formed from nitinol, stents may be constructed of any suitable stent material including, but not limited to stainless steel, Elgiloy, nickel, titanium, nitinol, shape memory polymers, other polymeric materials, etc.

Thermoplastic polymer materials which may be employed in forming the device include both elastomeric and non-elastomeric materials, examples of which include, but are not limited to, polyolefins such as metallocene catalyzed polyethylenes, polypropylenes, and polybutylenes, polycyclooctenes, and copolymers thereof; vinyl aromatic polymers such as polystyrene; vinyl aromatic copolymers such as styrene-isobutylene copolymers and butadiene-styrene copolymers; ethylenic copolymers such as ethylene vinyl acetate (EVA), ethylene-methacrylic acid and ethylene-acrylic acid copolymers where some of the acid groups have been neutralized with cations, for example zinc or sodium ions (commonly known as ionomers); alkyl acrylates and methacrylate polymers and copolymers, polyacetals; chloropolymers such as polyvinylchloride (PVC); fluoropolymers such as polytetrafluoroethylene (PTFE); polyesters such as polyethyleneterephthalate (PET); polyester-ethers; polyamides such as nylon 6 and nylon 6,6; polyamide ethers; polyethers; elastomers such as elastomeric polyurethanes and polyurethane copolymers; polycarbonates; methylmethacrylate N-vinylpyrrolidone copolymers; polyvinyl alcohol (PVA); poly(ethylene oxide) (PEO); and blends, mixtures and block or random copolymers of any of the foregoing.

Stent 10 may also optionally be formed at least partially, or entirely of a biodegradable or bioabsorbable polymer material. Examples include, but are not limited to, poly (alpha-hydroxy acid) polymers and copolymers, such as polymers and copolymers of glycolide including polyglycolide (PGA), poly(glycolide-co-lactide) (PGLA), and poly (glycolide-co-trimethylene carbonate (PGA/TMC; polymers and copolymers of polylactide (PLA) including poly-L-lactide (PLLA), poly-D-lactide (PDLA), poly-DL-lactide (PDLLA), poly(lactide-co-tetramethylene glycolide), poly (lactide-co-trimethylene carbonate), poly(lactide-co-delta-valerolactone), poly(lactide-co-epsilon-caprolactone), poly (glycine-co-DL-lactide) and poly(lactide-co-ethylene oxide); polydioxanone polymers such as asymmetrically 3,6-substituted poly-1,4-dioxane-2,5-diones; poly(beta-hydroxybutyrate) (PHBA) and copolymers of the same such as poly(beta-hydroxybutyrate-co-beta-hydroxyvalerate); polygluconate; poly(beta-hydroxypropionate) (PHPA); poly (beta-dioxanone)(PDS); poly(valerolactone); poly(caprolactone); polyester amides; polyesters of oxalic acid; polydihydropyranes; poly(alkyl-2-cyanoacrylate); polypeptides; poly(beta-maleic acid) (PMLA); poly(beta-alkanoic acid); tyrosine polycarbonates; tyrosine polyeysters; polyanhydrides; polyphosphoester; polyurethanes with degradable soft segments such as PLA, PLGA, and so forth; chitin polymers; and blends, mixtures, block, and dendrimers of the polymers. See, for example, commonly assigned US Patent Publication No. 2012/0123521, the entire content of which is incorporated by reference herein. This patent also illustrates various stent designs which can be employed herein.

Any stent can have a covering and the coverings are thus not limited to nitinol stents. Moreover, the stent need not be covered whatsoever, may be partially covered or may be fully covered.

Other suitable covering materials can be employed as well. Examples of other suitable covering materials include, but are not limited to, polyethylene, polypropylene, polyvinyl chloride, polytetrafluoroethylene, including expanded polytetrafluoroethylene (ePTFE), fluorinated ethylene propylene, fluorinated ethylene propylene, polyvinyl acetate, polystyrene, poly(ethylene terephthalate), naphthalene, dicarboxylate derivatives, such as polyethylene naphthalate, polybutylene naphthalate, polytrimethylene naphthalate and trimethylenediol naphthalate, polyurethane, polyurea, polyamides, polyimides, polycarbonates, polyaldehydes, polyether ether ketone, natural rubbers, polyester copolymers, styrene-butadiene copolymers, polyethers, such as fully or partially halogenated polyethers, and copolymers and combinations thereof. See, for example, commonly assigned U.S. Pat. No. 8,114,147, the entire content of which is incorporated by reference herein.

Figure 3:
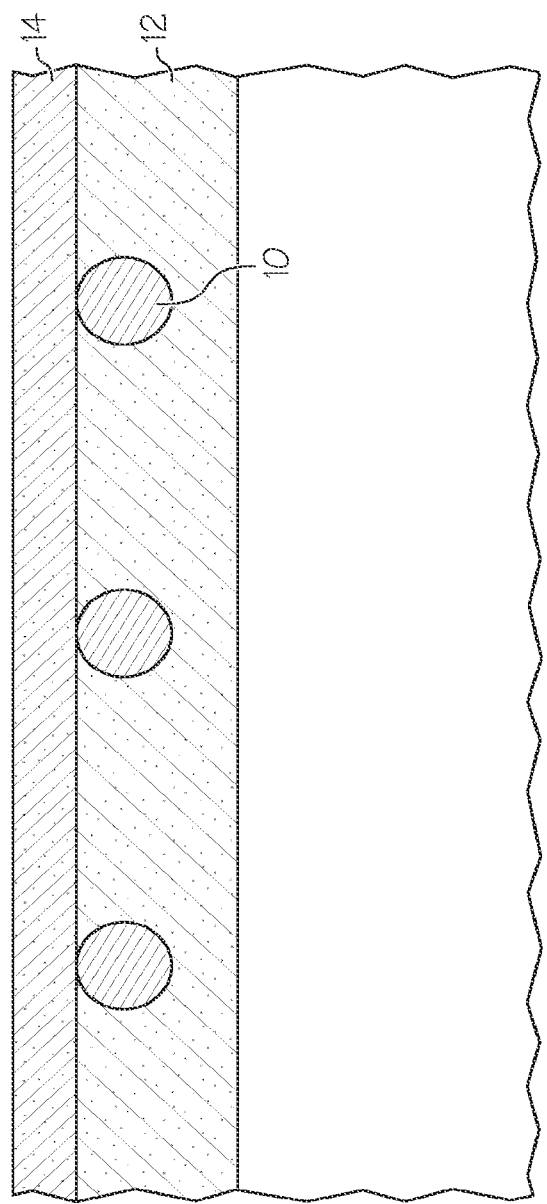
FIG. 3 is a perspective view of an exemplary stent on which the coatings may be employed.

Stent 10 further includes platelet-activated adhesive coating 14 as shown in cross-section in FIG. 3. This bioadhesive utilizes platelets as the main mechanism for adhesion. Platelet-activated adhesives exhibit non-adhesive properties until activated by coming into contact with a body lumen wall. A closed body lumen contains a heightened concentration of blood and therefore platelets in a centralized area. Once activated, the coating interacts by interlocking and bonding with tissue to create adhesion. Platelet-activated adhesives also have the capability to adhere through the mucous lining of the lumen wall. Platelet adhesion occurs when single platelets bind through specific membrane receptors to the cellular and extracellular matrix constituents. The response from the lumen wall to the adhesive coating can initiate a thrombus formation that permits the formation of a bridge-like connection between the stent and the swollen tissue at the stent deployment site.

For more on platelet adhesion, see http://circres.ahajournals.org/content/100/12/1673.full), the entire content of which is incorporated by reference herein.

The platelet-adhesive coating has the ability to begin absorbing into the tissue of the body lumen wall in about 2 to about 5 minutes and is fully absorbed in about 4 to about 6 weeks.

These platelet-activated adhesives promote regenerative cell growth while producing a biocompatible cover to protect the fresh growth cells from external damage and to prevent excessive amounts of scar tissue from developing in the lumen wall.

The process allows for the formation of a layer above the tissue lining the stent.

Platelet-adhesive coatings promote regenerative cell growth while producing a biocompatible cover to protect the fresh cells from external damage. The coating also prevents excessive amounts of scar tissue from developing in the tissue wall, and the naturally formed tissue will not incorporate into the stent coating which allows for atraumatic removal of the stent.

An alternative embodiment is to first apply the platelet-adhesive coating to the body lumen wall at the treatment site, and then deliver the stent to the treatment site.

Commercially available platelet-activated adhesives come in both gel and layered oxidized regenerated cellulose matrix formulations. Cellulose matrix formulations can bind immediately to tacky adhesive coatings such as a tacky silicone coating.

One example of a commercially available platelet-activated adhesives is Gelfoam® Absorbable Gelatin made by Pfizer Pharmaceuticals. This is a water-insoluble, non-elastic, porous, pliable product prepared from purified porcine skin. The gelatin has the ability to absorb and hold within its interstices approximately 45× its weight in blood and can expand up to 200% of its initial volume. When placed in soft tissues, it can be absorbed completely within four to six weeks without inducing excessive scar tissue.

Another example of a commercially available platelet-activated adhesive is Surgicel® Fibrillar™ Absorbable Hemostat made by Johnson & Johnson/Ethicon. This product is a soft, lightweight, and layered oxidized regenerated cellulose, which provides a matrix for platelet adhesion and aggregation. The product is able to melt directly into bleeding or swollen tissue. Surgicel® has a known shelf life of 3 years and can be stored at room temperature. It is able to absorb completely into tissue within 7-14 days without inducing excessive scar tissue.

Hemospray Absorbable Hemostatic Spray is also commercially available from Cook Medical. This is a single-use device, which is delivered through the channel of an endoscope and is sprayed toward the source of a bleed. When the powder from the spray comes in contact with blood, it is able to absorb water and forms a gel, which acts both cohesively and adhesively to create a stable mechanical barrier that adheres to and covers the bleeding site. It is a non-thermal, atraumatic treatment modality for achieving hemostasis.

Figure 4:
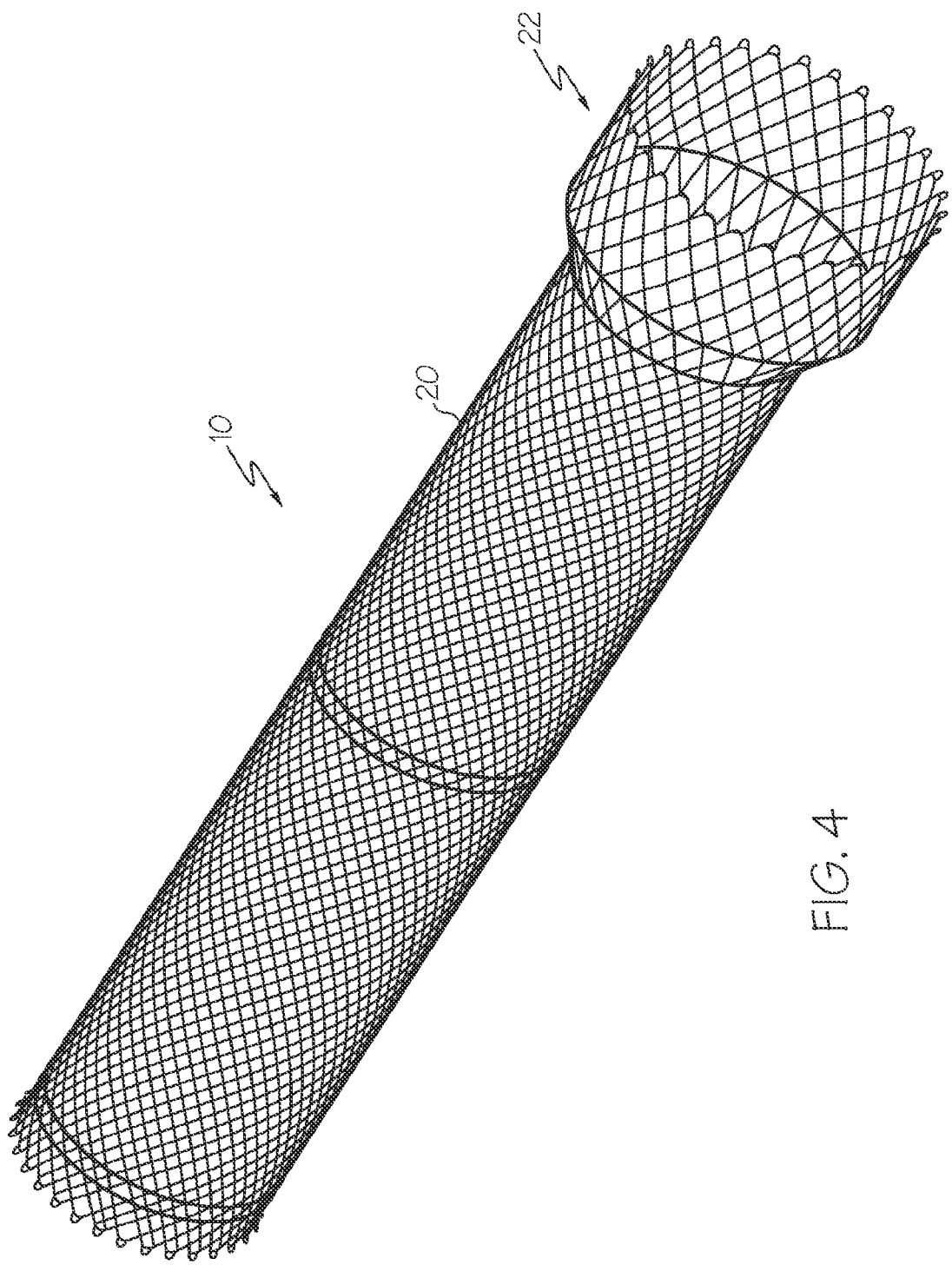
FIG. 4 is a perspective view of an endoscopic stent on which the coatings may be employed.

FIG. 4 is a perspective view of an endoscopic stent 10 on which the coatings may be employed. Stent 10 may be coiled or patterned as a braided or woven open network or fibers or filaments as disclosed, for example, in commonly assigned US Patent Publication No. 2012/0128793, the entire content of which is incorporated by reference herein. Stent 10 can also be laser cut.

Stent 10 can be self-expanding or balloon expandable.

In some embodiments, the stent has at least one flared end.

In one embodiment, stent 10 has a braided construction 20 and a flared proximal end 22. In this embodiment, stent 10 is an esophageal stent. Stent 10 may be formed of any suitable stent material including metallic and non-metallic materials as well as shape memory materials. Examples of suitable materials include, but are not limited to, shape memory alloys such as Nitinol®, other metallic materials such as stainless steel, tantalum, titanium, nickel-chrome, or cobalt-chromium alloys such as those sold under the tradename of Elgiloy®.

In one embodiment, the stent is a polymeric self-expanding stent formed from polyethylene terephthalate (PET) filaments having a silicone covering. These types of stents are commercially available from Boston Scientific Inc. located in Natick, Mass. under the tradename of Polyflex®.

Another example of a covered stent is a self-expanding nitinol stent formed of braided or woven wires and having a silicone covering. These types of stents are commercially available from Boston Scientific Inc. located in Natick, Mass. under the tradename of WallFlex®.

Another example of a covered stent is a self-expanding nitinol stent formed of braided or woven wires and having a polyurethane covering. These types of stents are commercially available from Boston Scientific Inc. located in Natick, Mass. under the tradename of Ultraflex®.

Figure 5:
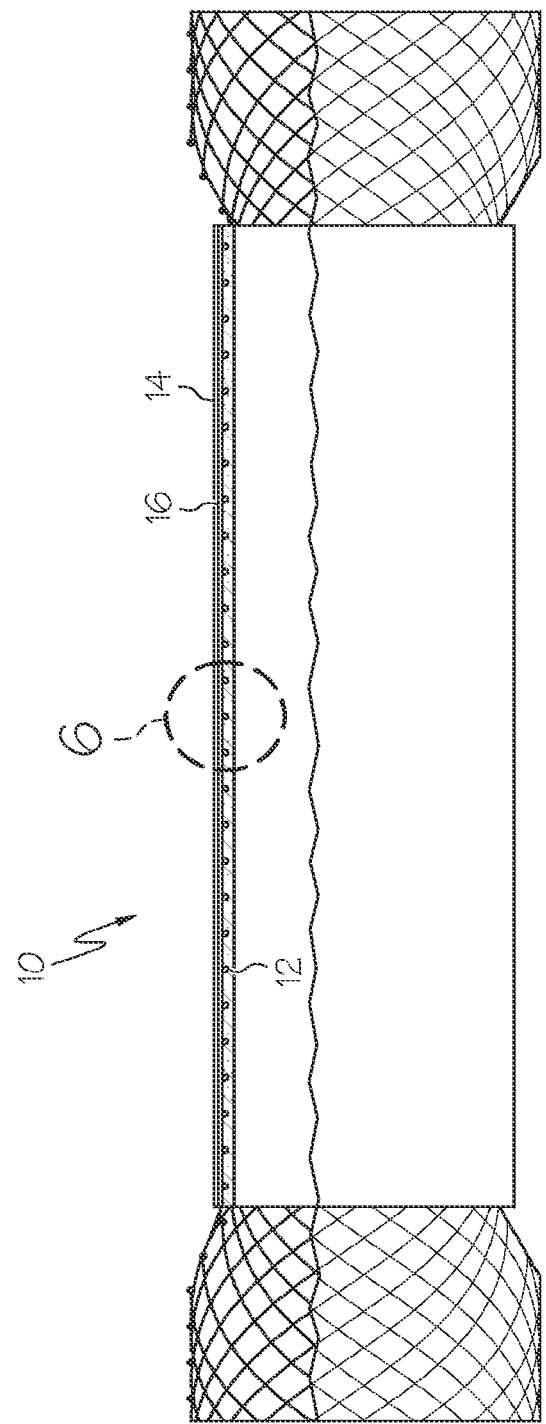
FIG. 5 is another exemplary embodiment of a stent on which the platelet-activated adhesive coating may be employed.

FIG. 5 is another exemplary embodiment of a stent 10 on which the platelet-activated adhesive coating 14 may be employed. In this embodiment, stent 10 is a self-expanding stent formed of a shape memory metal such as Nitinol® having a braided wire construction. Stent 10 further includes a silicone covering 12 and is partially embedded therein.

Stent 10 may be fully, substantially or partially covered or lined with a polymeric covering 12. The covering may be in the form of a tubular structure. Nonlimiting examples of useful polymeric materials include polyesters, polypropylenes, polyethylenes, polyurethanes, polynaphthalenes, polytetrafluoroethylenes, expanded polytetrafluoroethylene, silicone, copolymers thereof and mixtures or combinations thereof. Desirably, the polymeric covering 12 is silicone. Stents of this type are described in commonly assigned US Patent Publication Nos. 2006/0276887 and 2008/0009934, each of which is incorporated by reference herein in its entirety. The covering can also be disposed on the external surfaces of the stent 10, or disposed on both the internal and external surfaces of the stent 10.

In this embodiment, stent 10 additionally includes a second coating 16 of a tacky silicone or urethane disposed beneath the platelet-activated adhesive coating 14 for improving the adhesion of the platelet-activated adhesive coating 14 to the stent.

Figure 6:
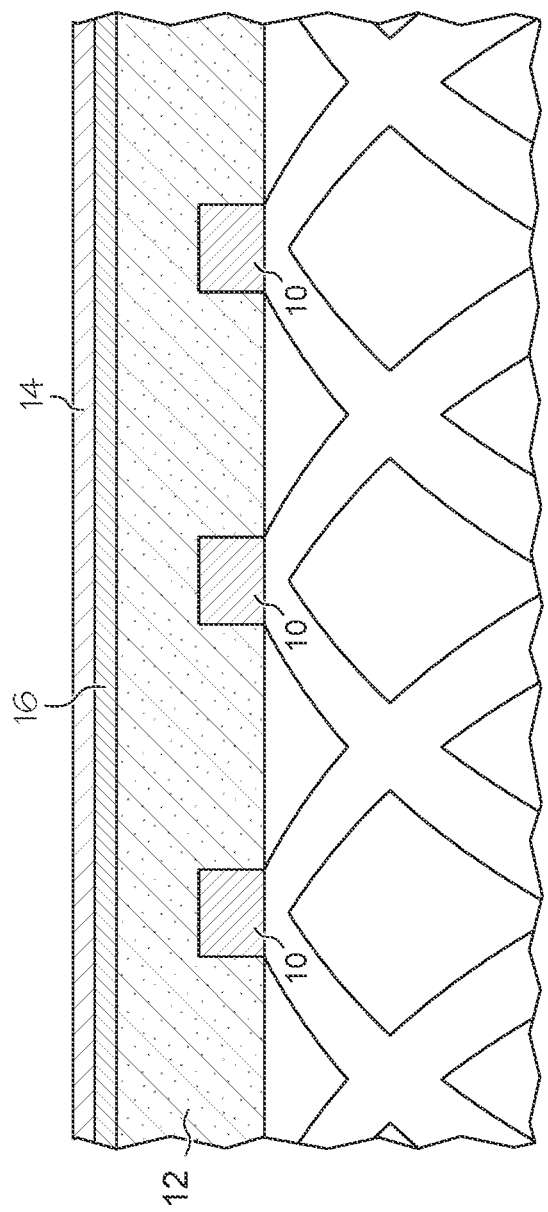
FIG. 6 is an enlarged view taken at section 6 in FIG. 5.

FIG. 6 is an enlarged view taken at section 6 in FIG. 5.

Figure 7:
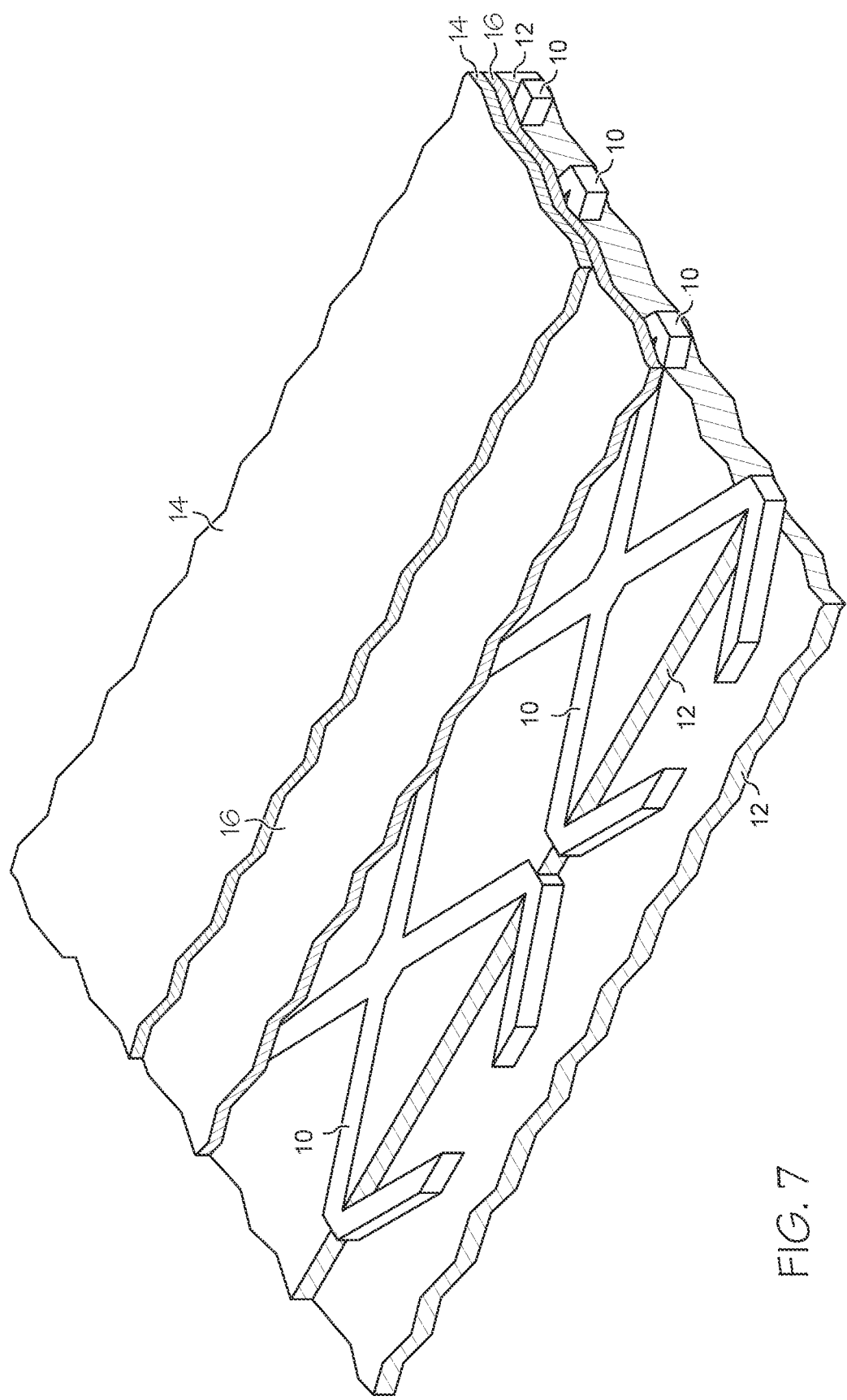
FIG. 7 is an enlarged perspective cross-section of a stent according to the invention illustrating a stent having a covering, a tacky silicone coating and platelet-activated adhesive coating.

FIG. 7 is an enlarged perspective cross-section of a stent according to the invention illustrating stent 10 with covering 12, tacky silicone coating 16 and platelet-activated adhesive coating 14.

All published documents, including all US patent documents and US patent publications, mentioned anywhere in this application are hereby expressly incorporated herein by reference in their entirety. Any copending patent applications, mentioned anywhere in this application are also hereby expressly incorporated herein by reference in their entirety. Citation or discussion of a reference herein shall not be construed as an admission that such is prior art.

The description provided herein is not to be limited in scope by the specific embodiments described which are intended as single illustrations of individual aspects of certain embodiments. The methods, compositions and devices described herein can comprise any feature described herein either alone or in combination with any other feature(s) described herein. Indeed, various modifications, in addition to those shown and described herein, will become apparent to those skilled in the art from the foregoing description and accompanying drawings using no more than routine experimentation. Such modifications and equivalents are intended to fall within the scope of the appended claims.

The invention claimed is:

1. A stent kit comprising:
   an expandable stent; and
   a platelet-activated adhesive configured to be applied to a body lumen wall and to initiate thrombus formation responsive to application to the body lumen.

2. The stent kit of claim 1, wherein the platelet-activated adhesive comprises bioabsorbable water-insoluble gelatin.

3. The stent kit of claim 1, wherein the platelet-activated adhesive comprises bioabsorbable hemostat.

4. The stent kit of claim 1, wherein the platelet-activated adhesive is a gel.

5. The stent kit of claim 1, wherein the platelet-activated adhesive is a layered oxidized regenerated cellulose matrix.

6. The stent kit of claim 1, wherein the expandable stent has a polymer covering disposed on at least an outer surface of the expandable stent.

7. The stent kit of claim 6, wherein the polymer covering is a silicone covering.

8. The stent kit of claim 7, wherein the expandable stent is completely embedded in the silicone covering.

9. The stent kit of claim 7, wherein the expandable stent further includes a tacky polymeric coating applied to an outer surface of the silicone covering.

10. The stent kit of claim 9, wherein the tacky polymeric coating comprises a tacky polyurethane polymer.

11. The stent kit of claim 1, wherein the expandable stent has at least one flared end portion.

12. The stent kit of claim 1, wherein the expandable stent is made of a polymer.

13. The stent kit of claim 12, wherein the polymer is biodegradable or bioabsorbable.

14. A stent kit comprising:
    an expandable stent at least partially embedded in a silicone covering, the expandable stent further having a tacky polymeric coating over the silicone covering; and
    a platelet-activated adhesive configured to be applied to a body lumen wall.

15. The stent kit of claim 14, wherein the platelet-activated adhesive comprises bioabsorbable water-insoluble gelatin.

16. The stent kit of claim 14, wherein the platelet-activated adhesive comprises bioabsorbable hemostat.

17. The stent kit of claim 14, wherein the platelet-activated adhesive is a layered oxidized regenerated cellulose matrix.

18. A method of implanting a stent comprising:
    applying a platelet-activated adhesive to a body lumen wall at a treatment site; and after applying the platelet-activated adhesive, then delivering a stent to the treatment site.

19. The method of claim 18, wherein the stent includes a silicone covering.

20. The method of claim 18, wherein the treatment site is in the esophagus.

* * * * *